United States Patent
Sleevi et al.

(10) Patent No.: US 10,301,611 B2
(45) Date of Patent: May 28, 2019

(54) PROCESS FOR REFOLDING RECOMBINANT CHYMOTRYPSIN

(71) Applicant: Merck Sharp & Dohme Corp., Rahway, NJ (US)

(72) Inventors: Mark C. Sleevi, Longmont, CO (US); Jack Lile, Aurora, CO (US); Bryn Grimison, Boulder, CO (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 8 days.

(21) Appl. No.: 15/526,779

(22) PCT Filed: Nov. 13, 2015

(86) PCT No.: PCT/US2015/060502
§ 371 (c)(1),
(2) Date: May 15, 2017

(87) PCT Pub. No.: WO2016/081288
PCT Pub. Date: May 26, 2016

(65) Prior Publication Data
US 2017/0342397 A1    Nov. 30, 2017

Related U.S. Application Data

(60) Provisional application No. 62/081,227, filed on Nov. 18, 2014.

(51) Int. Cl.
*C12N 9/50* (2006.01)
*C12N 9/52* (2006.01)
*C07K 1/14* (2006.01)
*C12N 9/76* (2006.01)

(52) U.S. Cl.
CPC .... *C12N 9/6427* (2013.01); *C12Y 304/21001* (2013.01)

(58) Field of Classification Search
CPC . C12N 9/00; C12N 15/57; C12N 9/50; C12N 9/52; C12P 21/06; C07K 1/14
See application file for complete search history.

(56) References Cited

U.S. PATENT DOCUMENTS

2012/0135460 A1    5/2012  Pridmore et al.

FOREIGN PATENT DOCUMENTS

| WO | WO9311240 | 6/1993 |
| WO | 200119970 | 3/2001 |
| WO | WO2008008975 | 1/2008 |

OTHER PUBLICATIONS

Verheyden et al., Expression of chymotrypsin in the thioredoxin reductase deficient mutant strain of *Escherichia coli* AD494 DE3 and purification via a fusion product wit a hexahistidine tail, Journal of Chromatography B Biomedical Sciences and Applicat, 2000, pp. 213-224, vol. 737.
Wang et al., Purification cDNA cloning and recombinant expression of chymotrypsin C from porcine pancreas, Acta Biochimica et Biophysica Sinica, 2011, No. 7, pp. 568-575, vol. 43.

*Primary Examiner* — Maryam Monshipouri
(74) *Attorney, Agent, or Firm* — John David Reilly; Laura M. Ginkel

(57) ABSTRACT

A process for refolding recombinant chymotrypsin produced from prokaryote host cells is described. In particular, the present invention provides a process for refolding recombinant chymotrypsin produced from *E. coli* is described.

19 Claims, No Drawings
Specification includes a Sequence Listing.

PROCESS FOR REFOLDING RECOMBINANT CHYMOTRYPSIN

CROSS REFERENCE TO RELATED APPLICATIONS

This application claims benefit of U.S. Provisional Application No. 62/081,227 filed Nov. 18, 2014, which is incorporated herein by reference in its entirety.

BACKGROUND OF THE INVENTION (1) Field of the Invention

This application is the National Stage of International Application No. PCT/US2015/060502 filed on Nov. 13, 2015, which claims benefit of U.S. Provisional Application No. 62/081,227 filed Nov. 18, 2014, each of which is incorporated herein by reference in its entirety.

(2) Description of Related Art

Chymotrypsin is a serine protease widely used in commercial processes for making various therapeutic proteins. Chymotrypsin preferentially cleaves peptide amide bonds where the carboxyl side of the amide bond (the P1 position) is a large hydrophobic amino acid (tyrosine, tryptophan, and phenylalanine). These amino acids contain an aromatic ring in their sidechain that fits into a 'hydrophobic pocket' (the S1 position) of the enzyme. It is activated in the presence of trypsin. These pancreatic enzymes are secreted through the pancreatic duct into the duodenum of the small intestine in response to a hormone signal generated when food passes from the stomach. They are not, however, synthesized in their final active form. Rather, they are made as slightly longer catalytically inactive molecules called zymogens. The names given to some of these zymogens include chymotrypsinogen, chymotrypsinogen, proelastase, and procarboxypeptidase. These zymogens must themselves be cleaved proteolytically to yield active enzymes.

Chymotrypsins have a variety of uses. They are useful for the characterization of other proteins as well as in the manufacturing process of other recombinant biological products. For example, small recombinant proteins are often expressed first as fusion proteins to facilitate their purification and enhance their stability. The fusion proteins can be engineered such that a leader sequence can be cleaved from the native protein sequence by chymotrypsin. Chymotrypsin has been used for the manufacture of insulin and insulin analogs and for the manufacture of various vaccine products.

Thus, there exists a need in the art for an efficient and inexpensive means to produce recombinant chymotrypsin which can then be used to safely and consistently manufacture other protein therapeutics, without unwanted cleavage products. Accordingly, the present invention provides an efficient and relatively inexpensive process to manufacture recombinant chymotrypsin.

BRIEF SUMMARY OF THE INVENTION

The present invention provides a method for making recombinant chymotrypsin from its zymogen chymotrypsinogen produced from a prokaryote host cell at high yield. The process allows for refolding to take place at much higher protein concentrations than has been previously reported and in the presence of a low molecular weight reducing agent without a low molecular weight oxidizing agent, i.e., without a low molecular weight redox pair. The process results in much higher refold efficiencies than has been previously attainable for chymotrypsin produced from a prokaryote host cell. The ability to achieve high refold efficiencies enables the production of a recombinant chymotrypsin at commercially relevant amounts.

Therefore, the present invention provides a process for refolding recombinant chymotrypsinogen produced from a prokaryote host cell comprising (a) providing the recombinant chymotrypsinogen in a solubilization solution comprising a chaotropic agent, a buffer agent, and a low molecular weight reducing agent in the absence of a low molecular weight oxidizing agent; and (b) infusing the solubilization solution comprising the recombinant chymotrypsinogen over time into a diluent comprising the chaotropic agent, buffer agent, and low molecular weight reducing agent in the absence of a low molecular weight oxidizing agent to provide a refold solution comprising the recombinant chymotrypsinogen at a concentration greater than 1 g/L or of about 1.5 g/L and incubating the refold solution comprising the recombinant chymotrypsinogen for a time sufficient for the recombinant chymotrypsinogen to refold into a conformation characteristic of native chymotrypsinogen and form the disulfide bonds characteristic of native chymotrypsinogen. In particular aspects, the prokaryote host cell is *E. coli*.

In particular embodiments of the process, the chaotropic agent in the solubilization solution is about five to 10 M or about 6.45 M. In particular aspects, the chaotropic agent in the refold solution is about 1.4 to 1.8 M. In particular aspects of the present invention, the chaotropic agent in the solubilization solution and the refold solution is guanidinium chloride.

In particular embodiments of the process, the low molecular weight reducing agent in the solubilization solution comprising the recombinant chymotrypsinogen is at a concentration sufficient to provide about 1 to 15 SH residues of the low molecular weight reducing agent per cysteine residue of the recombinant chymotrypsinogen. In particular embodiments of the process, the low molecular weight reducing agent in the solubilization solution comprising the recombinant chymotrypsinogen is at a concentration sufficient to provide about 2-3 or about 13 SH residues of the low molecular weight reducing agent per cysteine residue of the recombinant chymotrypsinogen.

In particular aspects of the process, the low molecular weight reducing agent in the refold solution comprising the recombinant chymotrypsinogen is at a concentration sufficient to provide about 1 to 30 SH residues of the low molecular weight reducing agent per cysteine residue of the recombinant chymotrypsinogen. In particular aspects of the process, the low molecular weight reducing agent in the refold solution comprising the recombinant chymotrypsinogen is at a concentration sufficient to provide about 2 or about 25 SH residues of the low molecular weight reducing agent per cysteine residue of the recombinant chymotrypsinogen. In particular aspects, the low molecular weight reducing agent is cysteine or cysteine hydrochloride or L-cysteine of L-cysteine hydrochloride. In particular aspects, the low molecular weight reducing agent is dithiothreitol (DTT).

In particular aspects of the process, the recombinant chymotrypsinogen comprises the amino acid sequence for porcine chymotrypsin or bovine chymotrypsin.

In particular aspects of the process, the solubilized recombinant chymotrypsinogen is obtained from inclusion bodies isolated from prokaryote host cells transformed with an expression vector comprising a nucleic acid molecule encoding the recombinant chymotrypsinogen and fermented under conditions for producing the recombinant chymotrypsinogen.

The present invention further provides a process for preparing recombinant chymotrypsin comprising (a) providing solubilized recombinant chymotrypsinogen in a solubilization solution comprising a chaotropic agent, a buffer agent, and a low molecular weight reducing agent in the absence of a low molecular weight oxidizing agent at a pH at about the pI of chymotrypsinogen or greater; (b) infusing the solubilization solution comprising the recombinant chymotrypsinogen over time into a diluent comprising the chaotropic agent, buffer agent, and low molecular weight reducing agent in the absence of a low molecular weight oxidizing agent at a pH of about the pI of chymotrypsinogen to provide a refold solution comprising the recombinant chymotrypsinogen at a concentration greater than 1 g/L and less than 12.5 g/L, or of about 1.5 g/L; (c) incubating the refold solution comprising the recombinant chymotrypsinogen for a time sufficient for the recombinant chymotrypsinogen to refold into a conformation characteristic of native chymotrypsinogen and form the disulfide bonds characteristic of native chymotrypsinogen; and (d) diluting the refold solution and incubating the diluted refold solution for a time sufficient for the recombinant chymotrypsinogen therein to auto-catalyze to provide the recombinant chymotrypsin.

In a further embodiment of the process, the recombinant chymotrypsin is subjected to a chromatography step to provide a recombinant chymotrypsin substantially free of tryptic peptides from the auto-catalysis of the recombinant chymotrypsinogen. In particular aspects, the chromatography is affinity chromatography, which may be performed on a matrix comprising benzamidine, for example, a matrix comprising benzamidine.

In further embodiments of the process, the recombinant chymotrypsin substantially free of peptides from the auto-catalysis is concentrated to provide a composition comprising the recombinant chymotrypsin at a concentration of about 20 to 80 mg/mL.

In particular embodiments of the process, the chaotropic agent in the solubilization solution is about five to 10 M or about 6.45 M. In particular aspects, the chaotropic agent in the refold solution is about 1.4 to 1.8 M. In particular aspects of the present invention, the chaotropic agent in the solubilization solution and the refold solution is guanidinium chloride.

In particular embodiments of the process, the low molecular weight reducing agent in the solubilization solution comprising the recombinant chymotrypsinogen is at a concentration sufficient to provide about 1 to 15 SH residues of the low molecular weight reducing agent per cysteine residue of the recombinant chymotrypsinogen. In particular embodiments of the process, the low molecular weight reducing agent in the solubilization solution comprising the recombinant chymotrypsinogen is at a concentration sufficient to provide about 2-3 or about 13 SH residues of the low molecular weight reducing agent per cysteine residue of the recombinant chymotrypsinogen.

In particular aspects of the process, the low molecular weight reducing agent in the refold solution comprising the recombinant chymotrypsinogen is at a concentration sufficient to provide about 1 to 30 SH residues of the low molecular weight reducing agent per cysteine residue of the recombinant chymotrypsinogen. In particular aspects of the process, the low molecular weight reducing agent in the refold solution comprising the recombinant chymotrypsinogen is at a concentration sufficient to provide about 2 or about 25 SH residues of the low molecular weight reducing agent per cysteine residue of the recombinant chymotrypsinogen. In particular aspects, the low molecular weight reducing agent is cysteine or cysteine hydrochloride or L-cysteine of L-cysteine hydrochloride. In particular aspects, the low molecular weight reducing agent is dithiothreitol (DTT).

In particular embodiments of the process, the buffer agent is ethanolamine. In particular aspects of the process, the recombinant chymotrypsinogen comprises the amino acid sequence for porcine chymotrypsin or bovine chymotrypsin.

In particular aspects of the process, the solubilized recombinant chymotrypsinogen is obtained from inclusion bodies isolated from prokaryote host cells transformed with an expression vector comprising a nucleic acid molecule encoding the recombinant chymotrypsinogen and fermented under conditions for producing the recombinant chymotrypsinogen. In particular aspects, the prokaryote host cell is *E. coli*.

The present invention further provides a process for preparing recombinant chymotrypsin comprising (a) incubating transformed prokaryote host cells with a nucleic acid molecule encoding a chymotrypsinogen in a suitable culture medium for a time sufficient for cell growth and the simultaneous or subsequent expression of the nucleic acid molecule encoding the chymotrypsinogen for the formation of inclusion bodies comprising the typsinogen; (b) isolating the inclusion bodies comprising the recombinant chymotrypsinogen from the transformed host cells; (c) solubilizing the inclusion bodies comprising the recombinant chymotrypsinogen in a solubilization solution comprising a chaotropic agent, a buffer agent, and a low molecular weight reducing agent in the absence of a low molecular weight oxidizing agent; (d) infusing the solubilization solution comprising the recombinant chymotrypsinogen over time into a diluent comprising the chaotropic agent, buffer agent, and low molecular weight reducing agent in the absence of a low molecular weight oxidizing agent to provide a refold solution comprising the recombinant chymotrypsinogen at a concentration greater than 1 g/L or of about 1.5 g/L; (e) incubating the refold solution comprising the recombinant chymotrypsinogen for a time sufficient for the recombinant chymotrypsinogen to refold into a conformation characteristic of native chymotrypsinogen and form the disulfide bonds characteristic of native chymotrypsinogen; and (f) diluting the refold solution and incubating the diluted refold solution for a time sufficient for the recombinant chymotrypsinogen therein to auto-catalyze to provide the recombinant chymotrypsin.

In a further embodiment of the process, the recombinant chymotrypsin is subjected to a chromatography step to provide a recombinant chymotrypsin substantially free of tryptic peptides from the auto-catalysis of the recombinant chymotrypsinogen. In particular aspects, the chromatography is affinity chromatography, which may be performed on a matrix comprising benzamidine, for example, a matrix comprising benzamidine.

In further embodiments of the process, the recombinant chymotrypsin substantially free of peptides from the auto-catalysis is concentrated to provide a composition comprising the recombinant chymotrypsin at a concentration of about 20 to 80 mg/mL.

In particular embodiments of the process, the chaotropic agent in the solubilization solution is about five to 10 M or about 6.45 M. In particular aspects, the chaotropic agent in the refold solution is about 1.4 to 1.8 M. In particular aspects of the present invention, the chaotropic agent in the solubilization solution and the refold solution is guanidinium chloride.

In particular embodiments of the process, the low molecular weight reducing agent in the solubilization solution comprising the recombinant chymotrypsinogen is at a concentration sufficient to provide about 1 to 15 SH residues of the low molecular weight reducing agent per cysteine residue of the recombinant chymotrypsinogen. In particular embodiments of the process, the low molecular weight reducing agent in the solubilization solution comprising the recombinant chymotrypsinogen is at a concentration sufficient to provide about 2-3 or about 13 SH residues of the low molecular weight reducing agent per cysteine residue of the recombinant chymotrypsinogen.

In particular aspects of the process, the low molecular weight reducing agent in the refold solution comprising the recombinant chymotrypsinogen is at a concentration sufficient to provide about 1 to 30 SH residues of the low molecular weight reducing agent per cysteine residue of the recombinant chymotrypsinogen. In particular aspects of the process, the low molecular weight reducing agent in the refold solution comprising the recombinant chymotrypsinogen is at a concentration sufficient to provide about 2 or about 25 SH residues of the low molecular weight reducing agent per cysteine residue of the recombinant chymotrypsinogen. In particular aspects, the low molecular weight reducing agent is cysteine or cysteine hydrochloride or L-cysteine of L-cysteine hydrochloride. In particular aspects, the low molecular weight reducing agent is dithiothreitol (DTT).

In particular embodiments of the process, the buffer agent is ethanolamine. In particular aspects of the process, the recombinant chymotrypsinogen comprises the amino acid sequence for porcine chymotrypsin or bovine chymotrypsin.

In particular aspects of the process, the solubilized recombinant chymotrypsinogen is obtained from inclusion bodies isolated from prokaryote host cells transformed with an expression vector comprising a nucleic acid molecule encoding the recombinant chymotrypsinogen and fermented under conditions for producing the recombinant chymotrypsinogen. In particular aspects, the prokaryote host cell is *E. coli*.

The present invention further provides a process for preparing recombinant chymotrypsin comprising (a) providing solubilized recombinant chymotrypsinogen in a solubilization solution comprising a chaotropic agent, a buffer agent, and a first low molecular weight reducing agent in the absence of a low molecular weight oxidizing agent at a pH of about the pI of chymotrypsinogen or greater; (b) infusing the solubilization solution comprising the recombinant chymotrypsinogen into a diluent comprising the chaotropic agent, buffer agent, and a second low molecular weight reducing agent in the absence of a low molecular weight oxidizing agent at a pH of about the pI of chymotrypsinogen to provide a refold solution comprising the recombinant chymotrypsinogen at a concentration greater than 1 g/L and less than 12.5 g/L, or of about 1.5 g/L; (c) incubating the refold solution comprising the recombinant chymotrypsinogen for a time sufficient for the recombinant chymotrypsinogen to refold into a conformation characteristic of native chymotrypsinogen and form the disulfide bonds characteristic of native chymotrypsinogen; and (d) diluting the refold solution and incubating the diluted refold mixture for a time sufficient for the recombinant chymotrypsinogen therein to auto-catalyze to provide the recombinant chymotrypsin.

In a further embodiment of the process, the recombinant chymotrypsin is subjected to a chromatography step to provide a recombinant chymotrypsin substantially free of tryptic peptides from the auto-catalysis of the recombinant chymotrypsinogen. In particular aspects, the chromatography is affinity chromatography, which may be performed on a matrix comprising benzamidine, for example, a matrix comprising benzamidine.

In further embodiments of the process, the recombinant chymotrypsin substantially free of peptides from the auto-catalysis is concentrated to provide a composition comprising the recombinant chymotrypsin at a concentration of about 20 to 80 mg/mL.

In particular embodiments of the process, the chaotropic agent in the solubilization solution is about five to 10 M or about 6.45 M. In particular aspects, the chaotropic agent in the refold solution is about 1.4 to 1.8 M. In particular aspects of the present invention, the chaotropic agent in the solubilization solution and the refold solution is guanidinium chloride.

In particular embodiments of the process, the first low molecular weight reducing agent in the solubilization solution comprising the recombinant chymotrypsinogen is at a concentration sufficient to provide about 2 to 3 SH residues of the low molecular weight reducing agent per cysteine residue of the recombinant chymotrypsinogen.

In particular aspects of the process, the first and second low molecular weight reducing agent in the refold solution comprising the recombinant chymotrypsinogen is at a concentration sufficient to provide about 2 SH residues of the low molecular weight reducing agent per cysteine residue of the recombinant chymotrypsinogen.

In particular aspects, the first low molecular weight reducing agent is dithiothreitol (DTT) and the second low molecular weight reducing agent is cysteine or cysteine hydrochloride or L-cysteine of L-cysteine hydrochloride.

In particular embodiments of the process, the buffer agent is ethanolamine. In particular aspects of the process, the recombinant chymotrypsinogen comprises the amino acid sequence for bovine chymotrypsin.

In particular aspects of the process, the solubilized recombinant chymotrypsinogen is obtained from inclusion bodies isolated from prokaryote host cells transformed with an expression vector comprising a nucleic acid molecule encoding the recombinant chymotrypsinogen and fermented under conditions for producing the recombinant chymotrypsinogen. In particular aspects, the prokaryote host cell is *E. coli*.

Definitions

As used herein, the term "chymotrypsin" refers to any polypeptide or protein that is capable of cleaving peptide chains mainly when the amino acid on the carboxyl side of the amide bond (the P1 position) is a large hydrophobic amino acid (tyrosine, tryptophan, and phenylalanine) and the amino acid on the amino side of the amide bond is any amino acid except for proline. Polypeptides having such enzymatic activity have Enzyme Commission designation EC 3.4.21.1. Thus, the term includes the various isoforms of chymotrypsin, including but not limited to, chymotrypsin A and chymotrypsin B. The term "chymotrypsin" further includes chymotrypsin C, which has the designation EC 3.4.21.2. Chymotrypsin C cleaves on the carboxyl side of the amide bond when the P1 amino acid is leucine, tyrosine, phenylalanine, methionine, tryptophan, glutamine, or asparagine and the amino acid on the amino side of the peptide bond is any amino acid except for proline.

As used herein, the term "chymotrypsinogen" refers to the zymogen form of the chymotrypsin. A zymogen (or proenzyme) is an inactive enzyme precursor. A zymogen requires a biochemical change (such as a hydrolysis reaction revealing the active site, or changing the configuration to reveal the active site) for it to become an active enzyme.

As used herein, the term, "heterologous expression" means that the protein is experimentally put into a cell that does not normally make (i.e., express) that protein.

Heterologous polypeptide or heterologous protein thus refers to the fact that the transferred DNA coding for a polypeptide or protein such as chymotrypsinogen was initially cloned from or derived from a different cell type or a different species from the recipient. For example, the gene encoding chymotrypsinogen can be made synthetically and then transferred into the host organism, which as native organism does not pro-duce that polypeptide or protein. Therefore, the genetic material encoding for the polypeptide or protein can be added to the recipient cell by recombinant cloning techniques. The genetic material that is transferred for the heterologous expression should be within a format that encourages the recipient cell to express the recombinant DNA as open reading frame (ORF) to synthesize a protein, i.e., it is put in an expression vector.

As used herein, the term, "polypeptide" refers to a molecule comprising a linear chain of amino acids or a molecule comprising two or more linear chains of amino acids covalently linked by one or more disulfide linkages.

As used herein, the term "protein" refers to a polypeptide, which has the ability to form into a specific conformation. In the context of the present invention, the terms polypeptide and protein may be used interchangeably for polypeptides of a specific length or conformation.

As used herein, the term "recombinant DNA" refers to the form of artificial DNA such as a synthetic DNA or cDNA, e.g. coding for chymotrypsinogen that is created through the introduction of the DNA into an organism such as *E. coli* for the purpose of expression of the polypeptide or protein encoded by the recombinant DNA.

As used herein, the term "recombinant protein" thus is a protein that is derived from the recombinant DNA by expression of the recombinant DNA in the host cell.

As used herein, the term "correctly folded" protein (synonymously: "native protein" or "protein in its native conformation") such as native chymotrypsinogen or native chymotrypsin refers to a molecule, which has the three dimensional conformation and disulfide bridges as found in the naturally occurring, biologically active protein.

DETAILED DESCRIPTION OF THE INVENTION

The present invention provides a method for making recombinant chymotrypsin from its zymogen chymotrypsinogen produced from a prokaryote host cell at high yield. The process allows for refolding to take place at much higher protein concentrations than has been previously reported in the art and in the presence of a low molecular weight reducing agent without a low molecular weight oxidizing agent, i.e., without a low molecular weight redox pair. In the art, it is typical for the refold process to be performed with a pair of reduced and oxidized low molecular weight thiol reagents (e.g., See US Pub Application No. 20120135460). The process results much higher refold efficiencies than has been previously attainable for chymotrypsin produced from a prokaryote host cell. The ability to achieve high refold efficiencies enables the production of a recombinant chymotrypsin at commercially relevant amounts. Recombinant chymotrypsin is preferred for use in the production of therapeutic products over animal derived chymotrypsin currently in use, particularly with respect to safety (absence of transmissible spongiform encephalopathies and other infectious agents) and lot-to-lot consistency.

In a typical process for preparing the recombinant chymotrypsin according to the present invention, a prokaryotic host cell is transformed with a nucleic acid molecule, which encodes the recombinant chymotrypsinogen, to provide a recombinant host cell. The recombinant chymotrypsinogen may be an inactive chymotrypsin precursor (zymogen), including derivatives or homologues of chymotrypsinogen or any chymotrypsin precursor that can be processed into an enzymatically active chymotrypsin product. The amino acid sequence of the encoded recombinant chymotrypsinogen may be that for a mammalian chymotrypsinogen, e.g., the amino acid sequence may be that for the human, bovine, porcine, ovine, or rat chymotrypsinogen. For example, the porcine chymotrypsinogen B may comprise the amino acid sequence shown in SEQ ID NO:1 or the chymotrypsin B sequence shown in SEQ ID NO:2.

For the expression of the recombinant chymotrypsinogen, the nucleic acid molecule encoding the recombinant chymotrypsinogen is incorporated by standard cloning techniques into an expression vector suitable for expressing the recombinant tryspsinogen in the host cell. The expression vector provides all elements necessary for expression of chymotrypsinogen in the host cell. Suitable expression vectors are commercially available and include standard expression vectors for expression in *E. coli* such as pQET7 available from Qiagen in which the gene encoding the recombinant chymotrypsinogen is expressed under control of the T7 promoter. Transformation of prokaryote host cells such as *E. coli* are well known in the art, for example, see Sambrook et al., Cold Spring Harbor Laboratory Press, Cold Spring Harbor, N.Y., 1998.

In particular embodiments, the expression vector encoding the recombinant trypsinogen may comprise a nucleic acid molecule encoding the recombinant trypsinogen comprising the amino acid sequence shown in SEQ ID NO:3 or 4.

The recombinant prokaryote host cell is cultivated under conditions that allow for growth of the recombinant prokaryote host cell to provide a multiplicity of the recombinant host cell and expression of the recombinant nucleic acid molecule encoding the recombinant chymotrypsinogen by formation of inclusion bodies. The recombinant prokaryotic host cell is typically cultivated in a medium suitable for growth of the host cell. Suitable liquid media for growing the host organism include synthetic media, full or half media. Media for cultivation of *E. coli* include Luria Broth (LB), 2×YT or, a fully synthetic medium based on a phosphate buffer, a nitrogen source like ammonium chloride, a carbon- and energy source like glucose or glycerol, trace elements, and an amino acid supplement to enhance growth (Korz et al., J. Biotech. 39: 59 (1994)).

After sufficient growth of the recombinant prokaryotic host cell, the cells are usually harvested, e.g. by filtration or centrifugation, and then disrupted to further isolate the recombinant chymotrypsinogen from the broken cells. Disruption may be achieved by high pressure homogenization using a high pressure cell such as a French press cell. Other methods for disrupting the host cells include enzymatic treatment with lysozyme and/or sonication. In a prokaryotic host such as *E. coli*, the recombinant chymotrypsinogen is usually present in the form of insoluble inclusion bodies. The inclusion bodies may be isolated or separated from the cellular debris by centrifugation.

The isolated inclusion bodies are then solubilized to obtain the recombinant chymotrypsinogen contained within the inclusion bodies. Solubilization of the inclusion bodies may be achieved by solubilizing the inclusion bodies in a solubilization solution comprising a chaotrophic agent, a buffer agent, and a low molecular weight reducing agent in the absence of a low molecular weight oxidizing agent. The solubilization solution does not comprise a redox pair comprising a low molecular weight reducing agent and a low molecular weight oxidizing agent. The pH of the solubilization solution is generally at a pH that is about the same as or greater than the pI for the chymotrypsinogen. In general, concentration of inclusion bodies is such that the chymotrypsinogen is at a high concentration, in particular a concentration of about 5 to 15 g/L, or 10 to 15 g/L, or about 12.5 g/L. The low molecular weight reducing agent is at a concentration that sufficient to provide about 1 to 15 or about 13 or about 2 to 3 SH residues of the low molecular weight reducing agent per cysteine residue of the chymotrypsinogen. The inclusion bodies are incubated at a temperature and a time sufficient to effect the solubilization of substantially all of the recombinant chymotrypsinogen to provide solubilized recombinant chymotrypsinogen. For example, the incubation may be for 20 to 180 minutes, or between 30 and 120 minutes, or between 45 and 90 minutes. Typically, incubation is performed under mild shaking or mixing.

In a particular embodiment, the chaotropic agent is urea or guanidinium chloride, which may be used at a concentration from about 6 to 8.5 M, or about 6.45 M. In particular embodiments, the buffer agent may be ethanolamine, which may be at a concentration from 50 to 200 mM, or about 180 mM. In particular embodiments, the low molecular weight reducing agent may be cysteine at a concentration of about 50 mM.

In particular embodiments, the low molecular reducing agent in the solubilization solution is cysteine. In particular embodiments, the low molecular weight reducing agent in the solubilization solution is dithiothreitol (DTT).

The solubilized recombinant chymotrypsinogen is not in the conformation or tertiary structure characteristic of native chymotrypsinogen and does not have the disulfide bonds characteristic for native chymotrypsinogen. Therefore, the solubilized recombinant chymotrypsinogen is subjected to a refold process wherein the solubilized chymotrypsinogen is allowed to refold into the conformation or tertiary structure characteristic of native insulin and form the disulfide bonds characteristic for native chymotrypsin.

Following solubilzation, the solubilization solution comprising the solubilized recombinant chymotrypsinogen is diluted over time to provide a refold solution comprising the solubilized recombinant chymotrypsinogen at a concentration of about 1 g/L to about 5 g/L or about 1.5 g/L, the chaotropic agent at a concentration that is about 25 to 30% of its concentration in the solubilization solution, and the low molecular weight reducing agent at a concentration sufficient to provide about 1 to 30 or about 25 or about 2 SH residues of the low molecular reducing agent per cysteine residue of the recombinant chymotrypsinogen. In particular embodiments, the low molecular weight reducing agent at a concentration sufficient to provide about 10 to 30 SH residues of the low molecular reducing agent per cysteine residue of the recombinant chymotrypsinogen. The refold solution does not include a low molecular weight oxidizing agent to provide a redox pair comprising the low molecular weight reducing agent and a low molecular weight oxidizing agent. The pH of the refold solution is at about the pI of the chymotrypsinogen, about 8.5 to 9.0. The refold solution is incubated at a time and temperature suitable for refolding of the solubilized chymotrypsinogen into its native conformation or tertiary structure, i.e., a conformation characteristic of native chymotrypsin and which has formed the disulfide bonds characteristic of native chymotrypsinogen. In particular embodiments, the incubation is at about 10 to 12° C. and the time is about 15 hours.

In particular embodiments, the solubilization solution comprising the solubilized recombinant chymotrypsinogen is infused into a diluent solution comprising the chaotropic agent, buffer agent, and low molecular weight reducing agent without a low molecular weight oxidizing agent at a concentration such that over time of the infusion to provide the refold solution comprising the solubilized recombinant chymotrypsinogen at a concentration of about 1 g/L to about 5 g/L or about 1.5 g/L, the chaotropic agent at a concentration that is about 25 to 30% of its concentration in the solubilization solution, and the low molecular weight reducing agent at a concentration sufficient to provide about 1 to 15 SH residues of the low molecular reducing agent per cysteine residue of the recombinant chymotrypsinogen. The volume of diluent solution is about 6 to 8 or about 7.34 volumes of the dilute per volume of solubilization solution. The rate of infusion may be constant and may be over a time period of about eight to 15 hours. While the infusion rate is dependent upon the total time of the infusion, the rate is constant throughout a given infusion.

In particular embodiments, the low molecular reducing agent in the refold solution is cysteine. In particular embodiments, the low molecular weight reducing agent in the refold solution is dithiothreitol (DTT). In particular embodiments, the low molecular weight reducing agent in the refold solution is a combination of cysteine and DTT. For example, the DTT and the cysteine may be at a concentration sufficient to provide about 1 to 30 SH residues per cysteine residue of the chymotrypsinogen. In a particular embodiment, the concentration provides about 2 SH residues per cysteine residue of the chymotrypsinogen.

In particular embodiments, the diluent may further comprise a calcium salt, e.g., calcium chloride, and/or an amino acid, e.g., arginine. Thus in particular embodiments, the refold solution comprises the solubilized recombinant chymotrypsinogen at a concentration of about 1 g/L to about 5 g/L or about 1.5 g/L, the chaotropic agent at a concentration that is about 25 to 30% of its concentration in the solubilization solution, the low molecular weight reducing agent at a concentration sufficient to provide about 10 to 30 SH residues of the low molecular reducing agent per cysteine residue of the recombinant chymotrypsinogen, an amino acid such as arginine, and a calcium salt such as calcium chloride.

In a particular aspect, the solubilized recombinant chymotrypsinogen is infused into a diluent solution comprising about 0.7 M guanidinium chloride, about 540 mM arginine, about 11 mM calcium chloride, and about 6 mM L-cysteine hydrochloride, and about 50 mM diluent buffer agent (e.g., Tris-HCl) at about pH 8.5 over about 8 to 15 hours to provide a refold solution. The final composition of the refold solution is about 1.5 g recombinant chymotrypsinogen/L in about 22 mM of the buffer agent, about 44 mM Tris, about 1.4 to 1.8 M guanidinium chloride, about 11.3 mM low molecular weight reducing agent, about 0 to 1000 mM or about 475 mM arginine and about 9.7 mM calcium chloride.

The pH for the refold solution may be about 8.5 to 9.0. Refolding is carried out at about 10 to 12° C. for a time sufficient for a substantial amount of the recombinant trysinogen to refold into the conformation similar to that of native trysinogen, which in particular embodiments may be about 15 hours.

The refold solution may further contain agents to prevent self-activation of chymotrypsinogen. Such an inhibitor can be, i.e. benzamidine, which is typically used in a concentration of about 1 to 100 mM, or about 5 to 10 mM.

The refolding chymotrypsinogen comprising the amino acid sequence of porcine chymotrypsin may be achieved in an embodiment wherein the low molecular weight reducing agent in the solubilization solution is at a concentration that provides about 13 SH residues per cysteine residue of the trysinogen and the refold solution provides about 25 SH residues per cysteine residue of the chymotrypsinogen.

The refolding chymotrypsinogen comprising the amino acid sequence of bovine chymotrypsin may be achieved in an embodiment wherein the low molecular weight reducing agent in the solubilization solution is at a concentration that provides about 2 to 3 SH residues per cysteine residue of the trysinogen and the refold solution provides about 2 SH residues per cysteine residue of the chymotrypsinogen. For example, the solubilization solution may comprise DTT and the refold solution may comprise a combination of cysteine and DTT. For example, the solubilization solution may comprise DTT at a concentration sufficient to provide about 2 to 3 SH residues per cysteine residue of the chymotrypsinogen and the refold solution may comprise a mixture of DTT and cysteine at a concentration sufficient to provide about 2 SH residues per cysteine residue of the chymotrypsinogen in the refold solution.

Processing of converting or activating the recombinant chymotrypsinogen into recombinant chymotrypsin is generally achieved by autocatalytic cleavage of the recombinant chymotrypsinogen into recombinant chymotrypsin or by incubation of chymotrypsinogen with the protease enterokinase. Suitable conditions for autocatalytic cleavage of chymotrypsinogen to chymotrypsin are known in the art (see for example, Kay and Kassell, J. Biol. Chem. 216: 6661 (1971)). Suitable conditions for proteolytic digestion of chymotrypsinogen with enterokinase are given, e.g. in Grant and Hermon-Taylor, Biochem. J. 147: 363 (1975). A suitable process for converting or activating the recombinant chymotrypsinogen to recombinant chymptrypsin may be performed essentially as follows.

The refolded recombinant chymotrypsinogen is concentrated about 10-fold by tangential flow filtration (TFF) and then diafiltered against three volumes of diafiltration buffer containing a buffer agent and a chaotropic agent, for example, 50 mM Tris, 2.5 M guanidinium chloride, pH 8.0. The filtration may be carried out at room temperature. The concentrated recombinant chymotrypsinogen is diluted three-fold with diluent buffer comprising a buffer agent and a calcium salt, for example, about 50 mM Tris, 75 mM calcium chloride, pH 8.0, which may be chilled to about 2-8° C. prior to use to provide primarily recombinant chymotrypsin, to provide a cleavage buffer to which is added sufficient trypsin to cleave the trypsinogen between amino acid residues 15 and 16 of the amino acid sequence shown in SEQ ID NO:1 or amino acids 23 and 24 of SEQ ID NO:3 or 4. For SEQ ID Nos:3 and 4, the chymotrypsin autocatalyzes cleavage of the amino acid sequence between amino acids 8 and 9. After addition of the diluent, the cleavage buffer is incubated for a time and temperature sufficient for the production of the recombinant chymotrypsin. For example, the cleavage may be carried out at a chilled temperature 2-8° C. for 9-13 hours (optimally 11 hours) without mixing.

In a particular embodiments, the cleavage solution has a pH of about 7 to 9, or 7.5 to 8.5 and calcium chloride at a concentration of between 10 and 100 mM, or about 75 mM. The solution is then typically incubated at about 2 to 37° C., or 20 to 37° C., or 2 to 8° C. until the recombinant chymotrypsinogen is completely converted to chymotrypsin.

Following conversion or activation of the recombinant chymotrypsinogen into recombinant chymotrypsin, the recombinant chymotrypsin is separated from process and product related impurities such as the peptides that arise during the cleavage step.

The cleavage solution comprising the recombinant chymotrypsin may be clarified via centrifugation and/or 0.2µ filtration. In general, to the cleavage solution comprising the recombinant chymotrypsin sufficient salt (e.g., sodium chloride) is added to produce a final concentration of about 50-500 mM salt (e.g., sodium chloride), or about 50 mM salt (e.g., sodium chloride). Following mixing and adjustment of the pH to 8.0, the solution is clarified by 0.2µ filtration to produce a clarified solution comprising the recombinant trypsinogen.

The recombinant chymotrypsinogen may be further purified from process-related impurities by methods known in the art, for example, ion exchange chromatography.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

| SEQ ID NO. | DESCRIPTION | SEQUENCE |
|---|---|---|
| 1 | Chymotrypsinogen B Sus scrufa | CGVPAIPPVLSGLSRIVNGENAVPGSWPWQVSLQDGT GFHFCGGSLISEDWVVTAAHCGVTTSDVVVAGEYDQA SDAEDIQVLKIAKVFKNPNFSLLTVRNDITLLKLATP ARFSRTVSAVCLPSASDDFPAGTLCATTGWGKTKYTA LKTPDKLQQAALPIVSSTVCKSYWGSKVTDVMICAGA SGVSSCMGDSGGPLVCQKNGAWTLVGIVSWGSSTCST TTPAVYARVTALIPWVQQILANN |
| 2 | Chymotrysin B Sus scrufa | IVNGENAVPGSWPWQVSLQDGTGFHFCGGSLISEDWV VTAAHCGVTTSDVVVAGEYDQASDAEDIQVLKIAKVF KNPNFSLLTVRNDITLLKLATPARFSRTVSAVCLPSA SDDFPAGTLCATTGWGKTKYTALKTPDKLQQAALPIV SSTVCKSYWGSKVTDVMICAGASGVSSCMGDSGGPLV CQKNGAWTLVGIVSWGSSTCSTTTPAVYARVTALIPW VQQILANN |

| SEQ ID NO. | DESCRIPTION | SEQUENCE |
|---|---|---|
| 3 | Modified chymotrypsin B (underlined leader of 6 to 8 amino acids wherein the amino acid preceding the C is F, W, or Y) | <u>MXXXXXXX</u>CGVPAIPPVLSGLSRIVNGENAVPGSWPW QVSLQDGTGFHFCGGSLISEDWVVTAAHCGVTTSDVV VAGEYDQASDAEDIQVLKIAKVFKNPNFSLLTVRNDI TLLKLATPARFSRTVSAVCLPSASDDFPAGTLCATTG WGKTKYTALKTPDKLQQAALPIVSSTVCKSYWGSKVT DVMICAGASGVSSCMGDSGGPLVCQKNGAWTLVGIVS WGSSTCSTTTPAVYARVTALIPWVQQILANN |
| 4 | Modified chymotrypsin B (underlined leader of 6 to 8 amino acids) | <u>MXXXXXXF</u>CGVPAIPPVLSGLSRIVNGENAVPGSWPW QVSLQDGTGFHFCGGSLISEDWVVTAAHCGVTTSDVV VAGEYDQASDAEDIQVLKIAKVFKNPNFSLLTVRNDI TLLKLATPARFSRTVSAVCLPSASDDFPAGTLCATTG WGKTKYTALKTPDKLQQAALPIVSSTVCKSYWGSKVT DVMICAGASGVSSCMGDSGGPLVCQKNGAWTLVGIVS WGSSTCSTTTPAVYARVTALIPWVQQILANN |

What is claimed:

1. A process for refolding recombinant chymotrypsinogen produced from a prokaryote host cell comprising:
   (a) providing the recombinant chymotrypsinogen at a concentration of about 5 to 15 g/L in a solubilization solution comprising a chaotropic agent, a buffer agent, and a low molecular weight reducing agent in the absence of a low molecular weight oxidizing agent, wherein the solubilization solution does not include a low molecular weight oxidizing agent to provide a redox pair comprising the low molecular weight reducing agent and a low molecular weight oxidizing agent; and
   (b) infusing the solubilization solution comprising the recombinant chymotrypsin over time into a diluent to provide a refold solution comprising the chaotropic agent at about 25% to 30% of its concentration in the solubilization solution, a buffer agent, and the low molecular weight reducing agent in the absence of a low molecular weight oxidizing agent to provide a refold solution comprising the recombinant chymotrypsinogen at a concentration between 1 and 5 g/L and incubating the refold solution for a time sufficient for the recombinant chymotrypsinogen to refold into a conformation characteristic of native chymotrypsinogen and form the disulfide bonds characteristic of native chymotrypsinogen, wherein the refold solution does not include a low molecular weight oxidizing agent to provide a redox pair comprising the low molecular weight reducing agent and a low molecular weight oxidizing agent.

2. The process of claim 1, wherein the chaotropic agent is guanidinium chloride.

3. The process of claim 1, wherein the chaotropic agent in the refold solution is about 1.4 to 1.8 M.

4. The process of claim 1, wherein the reducing agent is cysteine or cysteine hydrochloride.

5. The process of claim 1, wherein the low molecular weight reducing agent in the solubilization solution comprising the recombinant chymotrypsinogen is at a concentration sufficient to provide about 1 to 15 SH residues of the low molecular weight reducing agent per cysteine residue of the recombinant chymotrypsinogen.

6. The process of claim 1, wherein the low molecular weight reducing agent in the refold solution comprising the recombinant chymotrypsinogen is at a concentration sufficient to provide about 1 to 30 SH residues of the low molecular weight reducing agent per cysteine residue of the recombinant chymotrypsinogen.

7. The process of claim 1, wherein the recombinant chymotrypsinogen comprises the amino acid sequence for porcine or bovine chymotrypsin.

8. A process for preparing recombinant chymotrypsin comprising:
   (a) providing solubilized recombinant chymotrypsinogen at a concentration of about 5 to 15 g/L in a solubilization solution comprising a chaotropic agent, a buffer agent, and a first low molecular weight reducing agent in the absence of a low molecular weight oxidizing agent at a pH of about the pI of chymotrypsinogen or greater, wherein the solubilization solution does not include a low molecular weight oxidizing agent to provide a redox pair comprising the low molecular weight reducing agent and a low molecular weight oxidizing agent;
   (b) infusing the solubilization solution comprising the recombinant chymotrypsinogen into a diluent to provide a refold solution comprising the chaotropic agent at about 25% to 30% of its concentration in the solubilization solution, a buffer agent, and the first low molecular weight reducing agent in the absence of a low molecular weight oxidizing agent or a second low molecular weight reducing agent in the absence of a low molecular weight oxidizing agent at a pH of about the pI of chymotrypsinogen to provide a refold solution comprising the recombinant chymotrypsinogen at a concentration greater than 1 g/L and less than 12.5 g/L, or of about 1.5 g/L, wherein the refold solution does not include a low molecular weight oxidizing agent to provide a redox pair comprising the first or second low molecular weight reducing agent and a low molecular weight oxidizing agent;
   (c) incubating the refold solution comprising the recombinant chymotrypsinogen for a time sufficient for the recombinant chymotrypsinogen to refold into a conformation characteristic of native chymotrypsinogen and form the disulfide bonds characteristic of native chymotrypsinogen; and
   (d) diluting the refold solution and incubating the diluted refold solution for a time sufficient for the recombinant chymotrypsinogen therein to auto-catalyze to provide the recombinant chymotrypsin.

9. The process of claim 8, wherein the recombinant chymotrypsin is subjected to a chromatography step to remove peptides from the auto-catalysis of the recombinant chymotrypsinogen.

10. The process of claim 9, wherein the recombinant chymotrypsin obtained from the chromatography step is concentrated to provide a composition comprising the recombinant chymotrypsin at a concentration of about 20 to 80 mg/mL.

11. The process of claim 9, wherein the chromatography is affinity chromatography.

12. The process of claim 11, wherein the affinity chromatography is performed on a matrix comprising benzamidine.

13. The process of claim 8, wherein the recombinant chymotrypsinogen comprises the amino acid sequence for porcine or bovine chymotrypsin.

14. The process of claim 8, wherein the solubilized recombinant chymotrypsinogen is obtained from inclusion bodies isolated from prokaryote host cells transformed with an expression vector comprising a nucleic acid molecule encoding the recombinant chymotrypsinogen and fermented under conditions for producing the recombinant chymotrypsinogen.

15. The process of claim 14, wherein the prokaryote host cell is *E. coli*.

16. The process of claim 1, wherein the buffer agent is ethanolamine.

17. The process of claim 1, wherein the reducing agent is cysteine or cysteine hydrochloride.

18. The process of claim 8, wherein the buffer agent is ethanolamine.

19. The process of claim 8, wherein the reducing agent is cysteine or cysteine hydrochloride.

* * * * *

SEQUENCE LISTING

<160> NUMBER OF SEQ ID NOS: 4

<210> SEQ ID NO 1
<211> LENGTH: 245
<212> TYPE: PRT
<213> ORGANISM: Sus scrufa

<400> SEQUENCE: 1

```
Cys Gly Val Pro Ala Ile Pro Pro Val Leu Ser Gly Leu Ser Arg Ile
1               5                   10                  15

Val Asn Gly Glu Asn Ala Val Pro Gly Ser Trp Pro Trp Gln Val Ser
            20                  25                  30

Leu Gln Asp Gly Thr Gly Phe His Phe Cys Gly Gly Ser Leu Ile Ser
        35                  40                  45

Glu Asp Trp Val Val Thr Ala Ala His Cys Gly Val Thr Thr Ser Asp
    50                  55                  60

Val Val Val Ala Gly Glu Tyr Asp Gln Ala Ser Asp Ala Glu Asp Ile
65                  70                  75                  80

Gln Val Leu Lys Ile Ala Lys Val Phe Lys Asn Pro Asn Phe Ser Leu
                85                  90                  95

Leu Thr Val Arg Asn Asp Ile Thr Leu Leu Lys Leu Ala Thr Pro Ala
            100                 105                 110

Arg Phe Ser Arg Thr Val Ser Ala Val Cys Leu Pro Ser Ala Ser Asp
        115                 120                 125

Asp Phe Pro Ala Gly Thr Leu Cys Ala Thr Thr Gly Trp Gly Lys Thr
    130                 135                 140

Lys Tyr Thr Ala Leu Lys Thr Pro Asp Lys Leu Gln Gln Ala Ala Leu
145                 150                 155                 160

Pro Ile Val Ser Ser Thr Val Cys Lys Ser Tyr Trp Gly Ser Lys Val
                165                 170                 175

Thr Asp Val Met Ile Cys Ala Gly Ala Ser Gly Val Ser Ser Cys Met
            180                 185                 190

Gly Asp Ser Gly Gly Pro Leu Val Cys Gln Lys Asn Gly Ala Trp Thr
        195                 200                 205

Leu Val Gly Ile Val Ser Trp Gly Ser Ser Thr Cys Ser Thr Thr Thr
    210                 215                 220
```

```
Pro Ala Val Tyr Ala Arg Val Thr Ala Leu Ile Pro Trp Val Gln Gln
225                 230                 235                 240

Ile Leu Ala Asn Asn
            245
```

<210> SEQ ID NO 2
<211> LENGTH: 230
<212> TYPE: PRT
<213> ORGANISM: Sus scrufa

<400> SEQUENCE: 2

```
Ile Val Asn Gly Glu Asn Ala Val Pro Gly Ser Trp Pro Trp Gln Val
1               5                   10                  15

Ser Leu Gln Asp Gly Thr Gly Phe His Phe Cys Gly Gly Ser Leu Ile
                20                  25                  30

Ser Glu Asp Trp Val Val Thr Ala Ala His Cys Gly Val Thr Thr Ser
            35                  40                  45

Asp Val Val Ala Gly Glu Tyr Asp Gln Ala Ser Asp Ala Glu Asp
        50                  55                  60

Ile Gln Val Leu Lys Ile Ala Lys Val Phe Lys Asn Pro Asn Phe Ser
65                  70                  75                  80

Leu Leu Thr Val Arg Asn Asp Ile Thr Leu Leu Lys Leu Ala Thr Pro
                85                  90                  95

Ala Arg Phe Ser Arg Thr Val Ser Ala Val Cys Leu Pro Ser Ala Ser
                100                 105                 110

Asp Asp Phe Pro Ala Gly Thr Leu Cys Ala Thr Thr Gly Trp Gly Lys
            115                 120                 125

Thr Lys Tyr Thr Ala Leu Lys Thr Pro Asp Lys Leu Gln Gln Ala Ala
130                 135                 140

Leu Pro Ile Val Ser Ser Thr Val Cys Lys Ser Tyr Trp Gly Ser Lys
145                 150                 155                 160

Val Thr Asp Val Met Ile Cys Ala Gly Ala Ser Gly Val Ser Ser Cys
                165                 170                 175

Met Gly Asp Ser Gly Gly Pro Leu Val Cys Gln Lys Asn Gly Ala Trp
            180                 185                 190

Thr Leu Val Gly Ile Val Ser Trp Gly Ser Ser Thr Cys Ser Thr Thr
                195                 200                 205

Thr Pro Ala Val Tyr Ala Arg Val Thr Ala Leu Ile Pro Trp Val Gln
            210                 215                 220

Gln Ile Leu Ala Asn Asn
225                 230
```

<210> SEQ ID NO 3
<211> LENGTH: 254
<212> TYPE: PRT
<213> ORGANISM: Artificial sequence
<220> FEATURE:
<223> OTHER INFORMATION: modified chymotrypsin B with a leader of 6-8
      amino acids
<220> FEATURE:
<221> NAME/KEY: VARIANT
<222> LOCATION: (2)..(2)
<223> OTHER INFORMATION: X is any amino acid
<220> FEATURE:
<221> NAME/KEY: VARIANT
<222> LOCATION: (3)..(3)
<223> OTHER INFORMATION: X is any amino acid
<220> FEATURE:
<221> NAME/KEY: VARIANT
<222> LOCATION: (4)..(4)
<223> OTHER INFORMATION: X is any amino acid

```
<220> FEATURE:
<221> NAME/KEY: VARIANT
<222> LOCATION: (5)..(5)
<223> OTHER INFORMATION: X is any amino acid
<220> FEATURE:
<221> NAME/KEY: VARIANT
<222> LOCATION: (6)..(6)
<223> OTHER INFORMATION: X is any amino acid or absent
<220> FEATURE:
<221> NAME/KEY: VARIANT
<222> LOCATION: (7)..(7)
<223> OTHER INFORMATION: X is any amino acid or absent
<220> FEATURE:
<221> NAME/KEY: VARIANT
<222> LOCATION: (8)..(8)
<223> OTHER INFORMATION: X is F, W, or Y
<220> FEATURE:
<221> NAME/KEY: misc_feature
<222> LOCATION: (9)..(9)
<223> OTHER INFORMATION: Xaa can be any naturally occurring amino acid

<400> SEQUENCE: 3

Met Xaa Xaa Xaa Xaa Xaa Xaa Xaa Cys Gly Val Pro Ala Ile Pro
1               5                   10                  15

Pro Val Leu Ser Gly Leu Ser Arg Ile Val Asn Gly Glu Asn Ala Val
            20                  25                  30

Pro Gly Ser Trp Pro Trp Gln Val Ser Leu Gln Asp Gly Thr Gly Phe
        35                  40                  45

His Phe Cys Gly Gly Ser Leu Ile Ser Glu Asp Trp Val Val Thr Ala
    50                  55                  60

Ala His Cys Gly Val Thr Thr Ser Asp Val Val Ala Gly Glu Tyr
65                  70                  75                  80

Asp Gln Ala Ser Asp Ala Glu Asp Ile Gln Val Leu Lys Ile Ala Lys
                85                  90                  95

Val Phe Lys Asn Pro Asn Phe Ser Leu Leu Thr Val Arg Asn Asp Ile
            100                 105                 110

Thr Leu Leu Lys Leu Ala Thr Pro Ala Arg Phe Ser Arg Thr Val Ser
        115                 120                 125

Ala Val Cys Leu Pro Ser Ala Ser Asp Asp Phe Pro Ala Gly Thr Leu
    130                 135                 140

Cys Ala Thr Thr Gly Trp Gly Lys Thr Lys Tyr Thr Ala Leu Lys Thr
145                 150                 155                 160

Pro Asp Lys Leu Gln Gln Ala Ala Leu Pro Ile Val Ser Ser Thr Val
                165                 170                 175

Cys Lys Ser Tyr Trp Gly Ser Lys Val Thr Asp Val Met Ile Cys Ala
            180                 185                 190

Gly Ala Ser Gly Val Ser Ser Cys Met Gly Asp Ser Gly Gly Pro Leu
        195                 200                 205

Val Cys Gln Lys Asn Gly Ala Trp Thr Leu Val Gly Ile Val Ser Trp
    210                 215                 220

Gly Ser Ser Thr Cys Ser Thr Thr Pro Ala Val Tyr Ala Arg Val
225                 230                 235                 240

Thr Ala Leu Ile Pro Trp Val Gln Gln Ile Leu Ala Asn Asn
                245                 250

<210> SEQ ID NO 4
<211> LENGTH: 254
<212> TYPE: PRT
<213> ORGANISM: Artificial sequence
<220> FEATURE:
<223> OTHER INFORMATION: Chymotrypsin B with a 7 amino acid leader
```

-continued

```
<220> FEATURE:
<221> NAME/KEY: VARIANT
<222> LOCATION: (2)..(2)
<223> OTHER INFORMATION: X is any amino acid or absent
<220> FEATURE:
<221> NAME/KEY: VARIANT
<222> LOCATION: (3)..(3)
<223> OTHER INFORMATION: X is any amino acid
<220> FEATURE:
<221> NAME/KEY: VARIANT
<222> LOCATION: (4)..(4)
<223> OTHER INFORMATION: X is any amino acid
<220> FEATURE:
<221> NAME/KEY: VARIANT
<222> LOCATION: (5)..(5)
<223> OTHER INFORMATION: X is any amino acid
<220> FEATURE:
<221> NAME/KEY: VARIANT
<222> LOCATION: (6)..(6)
<223> OTHER INFORMATION: X is any amino acid
<220> FEATURE:
<221> NAME/KEY: VARIANT
<222> LOCATION: (7)..(7)
<223> OTHER INFORMATION: X is any amino acid or absent
<220> FEATURE:
<221> NAME/KEY: misc_feature
<222> LOCATION: (8)..(8)
<223> OTHER INFORMATION: Xaa can be any naturally occurring amino acid

<400> SEQUENCE: 4

Met Xaa Xaa Xaa Xaa Xaa Xaa Phe Cys Gly Val Pro Ala Ile Pro
1               5                   10                  15

Pro Val Leu Ser Gly Leu Ser Arg Ile Val Asn Gly Glu Asn Ala Val
            20                  25                  30

Pro Gly Ser Trp Pro Trp Gln Val Ser Leu Gln Asp Gly Thr Gly Phe
        35                  40                  45

His Phe Cys Gly Gly Ser Leu Ile Ser Glu Asp Trp Val Val Thr Ala
    50                  55                  60

Ala His Cys Gly Val Thr Thr Ser Asp Val Val Ala Gly Glu Tyr
65                  70                  75                  80

Asp Gln Ala Ser Asp Ala Glu Asp Ile Gln Val Leu Lys Ile Ala Lys
                85                  90                  95

Val Phe Lys Asn Pro Asn Phe Ser Leu Leu Thr Val Arg Asn Asp Ile
            100                 105                 110

Thr Leu Leu Lys Leu Ala Thr Pro Ala Arg Phe Ser Arg Thr Val Ser
        115                 120                 125

Ala Val Cys Leu Pro Ser Ala Ser Asp Asp Phe Pro Ala Gly Thr Leu
    130                 135                 140

Cys Ala Thr Thr Gly Trp Gly Lys Thr Lys Tyr Thr Ala Leu Lys Thr
145                 150                 155                 160

Pro Asp Lys Leu Gln Gln Ala Ala Leu Pro Ile Val Ser Ser Thr Val
                165                 170                 175

Cys Lys Ser Tyr Trp Gly Ser Lys Val Thr Asp Val Met Ile Cys Ala
            180                 185                 190

Gly Ala Ser Gly Val Ser Ser Cys Met Gly Asp Ser Gly Gly Pro Leu
        195                 200                 205

Val Cys Gln Lys Asn Gly Ala Trp Thr Leu Val Gly Ile Val Ser Trp
    210                 215                 220

Gly Ser Ser Thr Cys Ser Thr Thr Pro Ala Val Tyr Ala Arg Val
225                 230                 235                 240

Thr Ala Leu Ile Pro Trp Val Gln Gln Ile Leu Ala Asn Asn
                245                 250
```